(12) United States Patent
Bamberg et al.

(10) Patent No.: US 7,688,448 B2
(45) Date of Patent: Mar. 30, 2010

(54) THROUGH-CONTAINER OPTICAL EVALUATION SYSTEM

(75) Inventors: Eberhard Bamberg, Salt Lake City, UT (US); Brendan J. Corbin, Tewksbury, MA (US); Stacy Bamberg, Salt Lake City, UT (US); Charles Hawker, Salt Lake City, UT (US); William Roberts, Sandy, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 185 days.

(21) Appl. No.: 11/809,709

(22) Filed: Jun. 1, 2007

(65) Prior Publication Data

US 2008/0297769 A1    Dec. 4, 2008

(51) Int. Cl.
*G01N 21/00* (2006.01)
(52) U.S. Cl. .................. 356/436; 356/440; 356/433
(58) Field of Classification Search ......... 356/432–440, 356/39
See application file for complete search history.

(56) References Cited

U.S. PATENT DOCUMENTS

| | | | |
|---|---|---|---|
| 4,707,133 A * | 11/1987 | Roberts et al. ............... | 356/320 |
| 5,478,750 A | 12/1995 | Bernstein et al. | |
| 6,195,158 B1 | 2/2001 | Cadell et al. | |
| 6,315,955 B1 | 11/2001 | Klein | |
| 6,628,395 B2 | 9/2003 | Liu et al. | |
| 6,711,424 B1 | 3/2004 | Fine et al. | |
| 6,770,883 B2 | 8/2004 | McNeal et al. | |
| 6,791,674 B2 | 9/2004 | Kawano | |
| 7,356,364 B1 * | 4/2008 | Bullock et al. ............... | 600/310 |
| 2004/0241736 A1 | 12/2004 | Hendee et al. | |
| 2006/0154327 A1 | 7/2006 | Bachur, Jr. et al. | |
| 2008/0144005 A1 * | 6/2008 | Guiney et al. ................. | 356/39 |

OTHER PUBLICATIONS

International Search Report and Written Opinion for PCT/US2008/65575, mailed Nov. 25, 2008.

* cited by examiner

*Primary Examiner*—Hoa Q Pham
(74) *Attorney, Agent, or Firm*—Holme Roberts & Owen LLP

(57) ABSTRACT

An apparatus, and method of its use, to determine a characteristic of a fluid sample contained inside a closed container. The ratio of intensity for detected radiation (e.g., light), subsequent to its transmission through the container's walls and fluid in the container, at each of a reference wavelength and a measurement wavelength is compared to a predetermined value to make a determination of the fluid's characteristic. Desirably, the wavelengths are applied to the same location on the container to minimize a source of signal error. The reference wavelength is selected for its substantial lack of attenuation when transmitted through a known fluid composition. The measurement wavelength is selected for its predictive interaction (e.g., absorption) with the fluid.

21 Claims, 16 Drawing Sheets

| Peak wavelength | Luminous intensity | Viewing angle | Max. current |
|---|---|---|---|
| 565 nm | 0.8 cd | 8° | 20 mA |
| 572 nm | 3.0 cd | 8° | 20 mA |

Table 1

| Peak wavelength | Luminous intensity | Viewing angle | Max. current |
|---|---|---|---|
| 565 nm | 0.8 cd | 8° | 20 mA |
| 572 nm | 3.0 cd | 8° | 20 mA |

Table 2

US 7,688,448 B2

THROUGH-CONTAINER OPTICAL EVALUATION SYSTEM

TECHNICAL FIELD

The invention relates generally to determination of characteristics of a fluid contained in a vessel. In particular, the invention provides a photometric system operable to determine certain characteristics of a fluid sample by comparing one or more predetermined numeric values against a ratio of the intensity of light, or other radiation, measured at two characteristic wavelengths, wherein the intensities are measured subsequent to passing the radiation through walls of the container (and typically also through the fluid sample).

BACKGROUND

Many situations exist in which it is desirable to interrogate fluid samples to determine one or more properties of the fluid, or to gain insight for an evaluation or diagnosis. In particular, the medical industry generates and evaluates numerous fluid samples as a part of ordinary medical care. Certain laboratories currently process about 5,000 of such samples per day, with an expectation that the number of processed samples will double within 4 to 5 years. The sheer volume of samples to be characterized essentially dictates that some sort of automation in sample evaluation is necessary.

A fully automated sample characterization system has several important obstacles to overcome, including ensuring minimum/maximum sample volume and avoiding interferences in the sample and/or incorrect sample content. If the volume of a sample is insufficient, the probe of the analyzer may crash into the bottom of the tube. On the other hand, if the test tube is overfilled, spillage can occur once the cap is removed and the tube is moved around the track system through various robotic systems. Certain fluid samples can contain interferences such as lipemia, icterus, hemolysis, clots, etc. These occurrences may impede the various analyzers and consequently must be accounted for, and sometimes removed from the sample, before the test can be properly completed. Occasionally, a sample labeled as serum actually contains urine and vice versa. In such cases, the sample identification bar codes printed on the tube labels are incorrect, and the samples should be flagged for correction and removed from further processing.

The current state-of-the-art implements prescreening of test tubes for volume, interferences, and/or content, through tedious manual inspection. Each incoming sample is visually inspected for observed interferences. In those cases where labels that are attached to the outside of the tube impede a visual inspection, the technicians will remove the cap and look down into the tube. The need for manual inspection of the tubes can prevent an otherwise automated laboratory facility from increasing sample throughput to a desired daily total. In addition, the frequent need for opening samples exposes technicians to the unknown content of the test tube, may cause contamination of the sample, and may result in spillage from overfilled tubes. Furthermore, visual examination tends to rely on the color of the sample. In certain cases, a technician may not properly identify a sample as urine, which tends to have the same color as blood serum. In addition, the various levels of interferences such as lipemia and hemolysis sometimes produce subtle changes in color, which make visual inspection a significant challenge.

Body fluid samples to be characterized in medical procedures are typically placed into a test tube prior to being delivered to a test facility. Such test tubes are typically made from polypropylene and generally include at least one self-adhering label applied to the side of the tube. The label(s) permit a bar code to be associated with the sample for identification and tracking. Unfortunately, such labels are nonuniform, and present a source of almost random interference for a photometric fluid characterization system. Nonetheless, work has been done to provide photometric fluid characterizing systems that could potentially be modified and adapted to the instant sample verification and screening problem.

In U.S. Pat. No. 5,478,750, the contents of which are incorporated herein by this reference, Bernstein et al. disclose a photometric analyzer for measuring the concentration of substances found in a body fluid sample. This analyzer measures light absorption in the sample at a number of preselected frequencies. Typically, white light is directed through the sample to a pair of apertures that direct light from the sample through a plurality of beam splitters, interference filters, and associated photodetectors. The analyzer further includes means for performing automatic calibration and error checking. They disclose that the effect of random variations between measurements may be minimized by averaging repeated measurements of a given sample. A light wavelength of 850 nm is used as a reference, because while such wavelength is not absorbed by the sample, its intensity is affected to the same degree as the light having relevant characterization wavelengths. The intensity of light at 850 nm and a plurality of detection wavelengths of light passed through a test sample is compared to the corresponding intensity of light at 850 nm and the same plurality of detection wavelengths of light passed through a control sample to determine the degree of light absorption in the test sample due to presence of a known reaction product.

U.S. Pat. No. 6,711,424, the contents of which are incorporated herein by this reference, issued to Fine et al., discloses the use of optical measurement to determine parameter (s) in blood using at least two frequencies of light. The method can be applied to in vivo, and well as in vitro tests. Fine et al. disclose making a plurality of measurements, or continuous measurement spanning a period of time, subsequent to cessation of blood flow. The values obtained from the measurements can be plotted to determine a parametric slope. To determine the parametric slope aimed at determining a desired parameter of blood, at least two wavelengths are selected in accordance with the parameter to be determined. Fine et al. disclose determination of concentration of a substance in a patient's blood by comparing the obtained parametric slope to predetermined calibration curves.

U.S. Pat. No. 6,770,883, the contents of which are incorporated herein by this reference, issued to Mc Neal et al., discloses a method and apparatus for detecting the vertical position of the interfaces between blood cells, plasma, etc., and separation gel in test tubes that may be covered by labels. Their method and apparatus requires shining light having two wavelengths through a test tube to determine an elevation of the interfaces. The first wavelength is transmitted by serum, plasma, labels and the material but substantially blocked by the cells. The second wavelength is substantially blocked by serum, plasma, and cells, but substantially transmitted by the material and labels. The test tube is moved vertically with respect to the light beams, and changes in detected transmission through the tube indicate the location(s) of the interfaces.

U.S. Pat. No. 6,195,158 B1, the contents of which are incorporated herein by this reference, describes an optical scanning system based on an array of LEDs that emit light between 400 and 2500 nm. The length of the array corresponds to the length of the tube such that the entire tube is illuminated. The transmitted light is received on the opposite side of the tube by silicon detectors. By measuring the absorption of different wavelengths and comparing these measurements to values that were obtained through calibration measurements and using statistical analysis, the following parameters can be obtained: height of fluid level, hemoglobin, total bilirubin, and lipids. Also measured is the temperature of the specimen, as well as its type (urine vs. plasma vs. serum).

In United States Patent application No. 2004/0241736, the contents of which are incorporated herein by this reference, Hendee et al. disclose methods and structures adapted to determine one or more attributes in a fluid sample from a spectrum of the sample. Their apparatus includes a light source that can deliver light comprising a plurality of wavelengths to the optical sampling apparatus, a collector that collects light that has interacted with the sample, a spectrometer, and a processor. In general terms, their light source generates infrared light that is directed to the sampling apparatus, where the light interacts with the biological sample. The optical source can optionally comprise a plurality of narrow wavelength devices, such as light-emitting diodes or laser diodes. The exiting light is directed to a spectrometer that yields an absorbance spectrum. The optical measurement system processes the absorbance spectrum using a multivariate calibration model to yield measurements of attributes of the sample, e.g., constituents of a blood sample.

Additional photometric, or optically based, fluid interrogation systems are disclosed in the patent literature. See, e.g., U.S. Pat. Nos. 6,195,158; 6,315,955; 6,628,395; and 6,791,674. Other relevant published United States utility Patent applications may include 2006/0154327. The entire disclosures of all of the aforementioned patents and patent applications are hereby incorporated as though set forth herein, in their entirety, for their disclosures of structure and methods related to radiologically interrogating fluid samples.

To facilitate increased automation of fluid sample testing, and particularly for body fluid sample testing, an improved fully automated system that can prescreen unopened test tubes for sample content and volume is desired. In addition, the prescreening desirably would include the scanning and identification of different anticoagulants such as citrate, EDTA, heparin, or fluoride, which presently cannot be detected through visual inspection, but may have an effect on the sample analysis procedure and/or result.

BRIEF SUMMARY OF THE INVENTION

An apparatus, and method of its use, to determine a characteristic of a fluid sample contained inside a closed container. The apparatus includes a radiation structure, intensity detector structure, and comparison structure. A first embodiment structured according to certain principles of the instant invention includes first and second radiation structure. An operable first radiation structure is configured and arranged to direct first emitted radiation through the container at a first location for reception of first transmitted radiation by a first intensity detector to obtain a first transmitted intensity. Desirably, the first emitted radiation includes a characteristic first wavelength selected as a reference based upon its substantial lack of attenuation when transmitted through a known fluid composition. An operable second radiation structure is configured and arranged to direct second emitted radiation through the container for reception of second transmitted radiation by the first intensity detector to obtain a second transmitted intensity. Desirably, the second emitted radiation includes a characteristic second wavelength that is distinguishable from the characteristic first wavelength, and is selected as a measurement tool based upon its predictive attenuation when transmitted through the same known fluid composition.

In addition, it is desirable for the first and second emitted radiation to be applied to the container at the same location. One currently preferred arrangement of first radiation structure and second radiation structure includes a first beam splitter in common, with the first beam splitter being arranged to cast first and second emitted radiation onto the same location.

An operable comparison structure is adapted to compare a first intensity ratio, of the first and second transmitted intensity, against a predetermined value. Sometimes, the intensity ratio includes division of the first transmitted intensity by the second transmitted intensity. Other times, the intensity ratio includes division of the second transmitted intensity by the first transmitted intensity.

A second embodiment structured according to certain principles of the instant invention includes third and fourth radiation structures. An operable third radiation structure maybe configured and arranged to direct third emitted radiation through the container at a second location effective to obtain a third transmitted intensity, where the second location is disposed at a container elevation that is different from the first location. An operable fourth radiation structure may be configured and arranged to direct fourth emitted radiation through the container at the second location effective to obtain a fourth transmitted intensity. In certain cases, the first emitted radiation and the third emitted radiation share the same characteristic first wavelength. In addition, the second emitted radiation and the fourth emitted radiation may share the same characteristic second wavelength. One currently preferred interrogation system includes a third radiation structure and fourth radiation structure having a second beam splitter in common. Such second beam splitter is desirably arranged to cast the third and fourth emitted radiation onto the same second location. Typically, the third and fourth transmitted radiations are received by a second intensity detector.

For data manipulation to determine a fluid characteristic, the comparison structure may be adapted to compare first data, comprising the second transmitted intensity, to second data, comprising the fourth transmitted intensity. Such data manipulation may be used to indicate presence of a desired fluid level in the container. Another operable way to indicate presence of fluid in the container is by comparing the first intensity ratio against a second intensity ratio, of the third and fourth transmitted intensity. It is also within contemplation alternatively to provide emission-directing structure adapted to move the container relative to the first intensity detector effective to permit detecting radiation transmitted through the container at a second elevation to verify a desired fluid level in the container.

A method for using an interrogation apparatus structured according to certain principles of the instant invention generally includes the steps of: disposing the container in position for interrogation by radiation; separately applying first emitted radiation and second emitted radiation, in any order, to the first location; obtaining a first numeric value corresponding to the first transmitted radiation and a second numeric value corresponding to the second transmitted radiation; calculating a first ratio of the first numeric value and the second numeric value; and comparing the first ratio to a predetermined value to make a determination about a fluid characteristic. Data manipulation may include dividing the first numeric value by the second numeric value, or dividing the second numeric value by the first numeric value.

Another method for using interrogation apparatus structured according to certain principles of the instant invention includes the steps of: disposing the container in position for interrogation by radiation; separately applying the first emitted radiation and the second emitted radiation, in any order, to the first location; obtaining a first numeric value corresponding to the first transmitted radiation and a second numeric value corresponding to the second transmitted radiation; separately applying the third emitted radiation and the fourth emitted radiation, in any order, to the second location; obtaining a third numeric value corresponding to the third transmitted radiation and a fourth numeric value corresponding to the fourth transmitted radiation; calculating a first ratio of the first numeric value and the second numeric value; and comparing the first ratio to a predetermined value to make a determination about a fluid characteristic. Such method may further include calculating a second ratio of the third numeric value and the fourth numeric value; and comparing the first ratio to the second ratio to make a determination about a fluid characteristic.

BRIEF DESCRIPTION OF THE SEVERAL VIEWS OF THE DRAWINGS

In the drawings, which illustrate what are currently considered to be the best modes for carrying out the invention.

DETAILED DESCRIPTION OF THE ILLUSTRATED EMBODIMENTS

Figure 1:
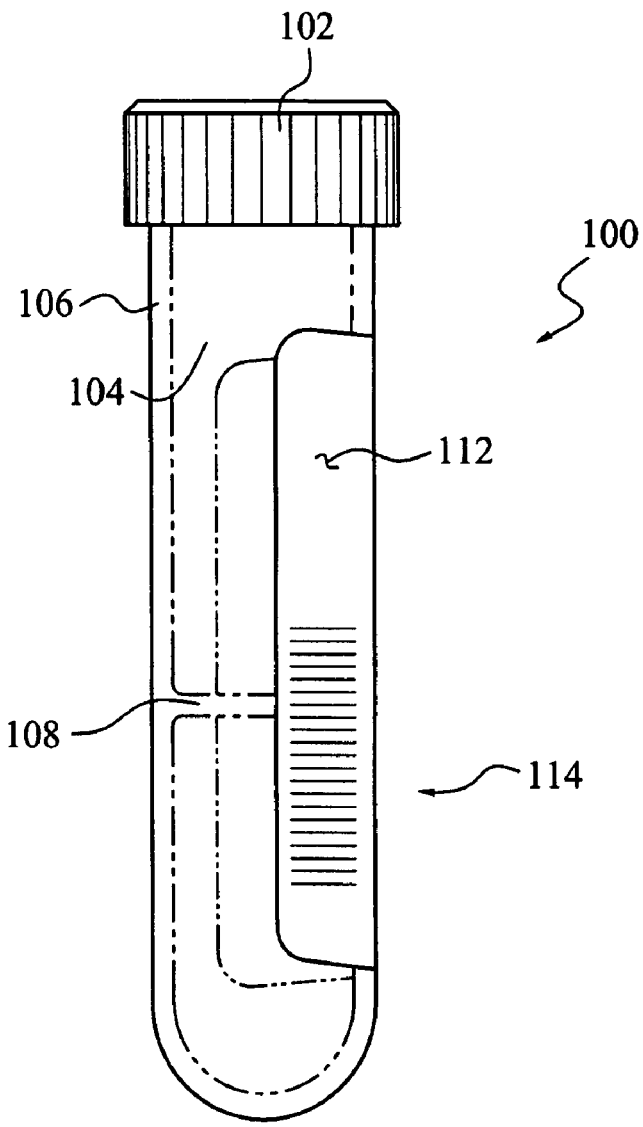
FIG. 1 is a view in elevation of a representative and operable sample container, including an identification label.

A workable container in which to hold a fluid sample for interrogation by a system constructed according to certain principles of the instant invention is illustrated in FIG. 1, and generally indicated at 100. Container 100 may be characterized as a test tube having a removable cap 102 that is structured to provide a fluid-resistant seal for chamber 104 in which the fluid sample is carried. As illustrated, chamber 104 is additionally bounded by cylindrical wall 106 and false bottom 108. Of course, alternative and operable containers may be arranged in different configurations, such as without a false bottom, or having other shapes and cross-sections. In general, a sample container will be configured to cooperate with transporting structure (not illustrated) of an automated sample testing or evaluation system.

One currently preferred sample container is made from polypropylene, and is well known and commonly used in processing and evaluating medical samples. In general, the sample container material may be manufactured from substantially any suitable fluid-resistant container material capable of transmitting radiation through its walls, such as a soda-lime, borosilicate, Pyrex, RTM, or other glass or a polypropylene, polymethylpentene, polycarbonate, or other medical-grade plastic, and the like.

Figure 2:
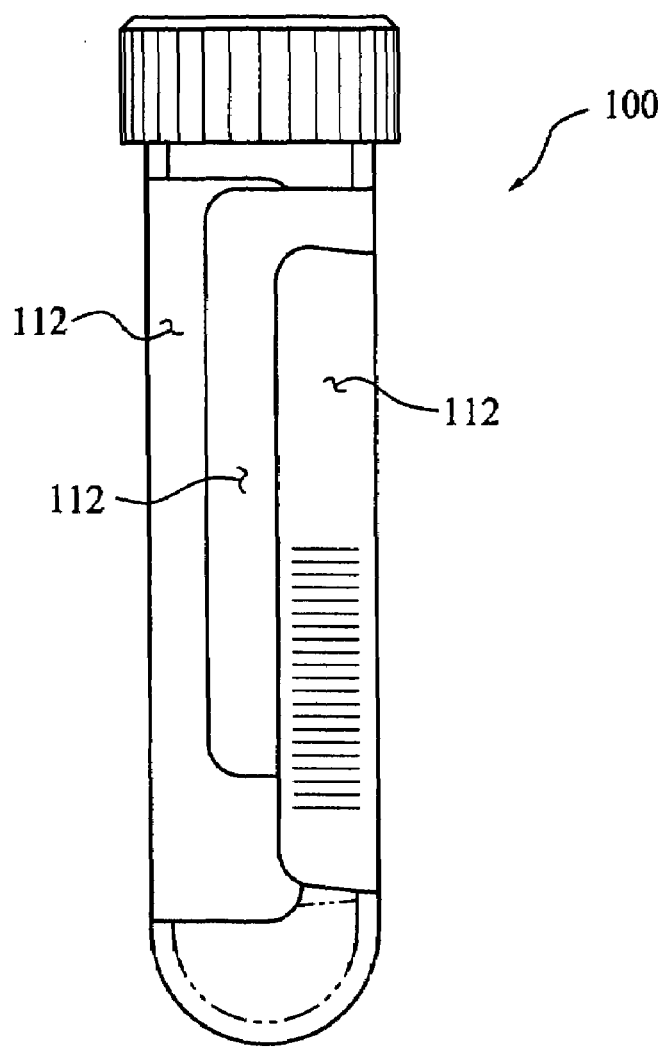
FIG. 2 is a view in elevation of a sample container such as illustrated in FIG. 1, but including a plurality of identification labels.

Container 100 illustrated in FIG. 1 includes a label 112 applied to an exterior surface of wall 106. Label 112 may be made from paper, or more commonly, polypropylene or other polymer film. Such label 112 typically provides tracking and identification information about the sample, such as sample number, constituent fluid, and patient identification. At least certain of such information desirably are maintained confidential, which can be accomplished by use of a bar code, generally indicated at 114, which is printed on the label 112. As illustrated in FIG. 2, sometimes a container 100 includes a plurality of labels 112 adhered to the wall 106. In any case, a sample container can be expected to have a variable number of labels, typically between zero and six, or even more in certain cases.

The presence of one or more label causes additional absorption of radiation applied to the container, and can represent a source of substantially random error in optically based interrogation of a sample using certain prior art techniques. For example, repetitive accuracy for the prior art technique in which presence or absence of fluid is detected simply based on absolute intensity of transmitted light at a specific wavelength is frustrated by the random absorption caused by an unknown number of labels. The present system avoids such random error, in part, by comparing a ratio of intensity of transmitted light at two wavelengths, as will be described in detail below.

Figure 3:
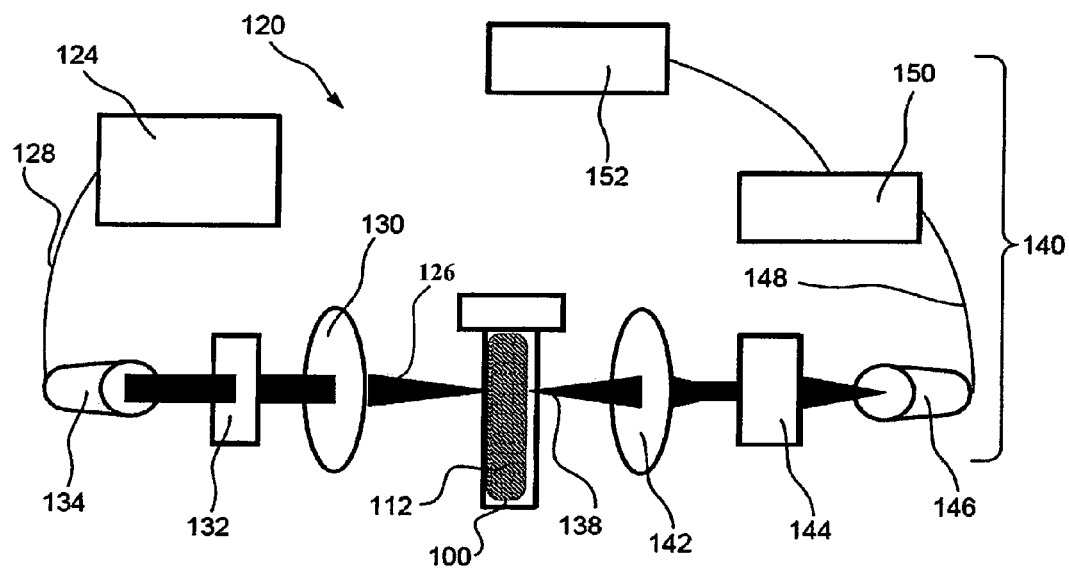
FIG. 3 is a schematic illustrating certain details of an operable arrangement to collect data for practice of a method of use according to certain principles of the instant invention.

Structure of an operable sample interrogation system, generally indicated at 120, which is constructed according to certain principles of the instant invention, is illustrated in FIG. 3. A source of radiation 124, such as one or more light bulbs, arc lamps, flash bulbs, LEDs, lasers, or the like, is arranged to apply emitted radiation 126 having at least two different and distinguishable wavelengths to a sample container 100. In general terms, radiation structure is configured and arranged to direct first emitted radiation 126 through a container 100 at a first location. Such radiation structure can include a plurality of elements; variably and/or optionally including one or more source of radiation 124, fiber optic cable 128, lens 130, filter 132, collimator 134, beam splitter, mirror, and the like. The emitted radiation 126 may interact with the fluid sample, container 100, and label(s) 112, resulting in a transmitted output that may be characterized as transmitted radiation 138. An intensity detector system, such as generally indicated at 140, is then used to obtain a transmitted intensity of one or more characteristic wavelengths of transmitted radiation 138.

For purpose of this disclosure, radiation may be described as having a wavelength, or characteristic wavelength. Such is intended, in certain instances, to encompass radiation spanning a range about a single recited wavelength. For example, a white light source can be applied through a filter system constructed to permit radiation having a restricted range of wavelengths to pass therethrough. A representative wavelength selected from such restricted range may be used as a characteristic wavelength to denote such emitted radiation. Certain intensity detectors may be arranged to detect the overall intensity of the entire spectrum of wavelengths in the restricted range of radiation that has been transmitted through a fluid sample, thereby providing an output denoting the transmitted intensity of such characteristic wavelength. Of course, in certain cases, such as when using a very high quality laser radiation source that emits radiation at substantially only a single wavelength, the characteristic wavelength simply applies over a more narrow range of wavelengths, such as a single wavelength. In other cases, the transmitted intensity of a single wavelength may be obtained from a suitably constructed detector, irrespective of the range of transmitted wavelengths received by the detector. It is believed that the proper scope encompassed by the terms "wavelength" and "characteristic wavelength" is logically determinable in context.

With continued reference to FIG. 3, the detector system 140 may include variably and/or optionally one or more lens 142, filter arrangement 144, collimator 146, and/or fiber optic cable 148. As illustrated, detector system 140 also may include a spectrum analyzer 150, CCD, or other intensity-obtaining device, which is adapted to transmit intensity data for one or more desired wavelength to comparison structure, such as the illustrated computer 152. The computer 152 is one device that is operable to manipulate the intensity data to determine a characteristic of the fluid sample.

It is also within contemplation that certain fluid characterizing systems structured according to certain principles of the invention could include data manipulation to characterize a fluid property, where the data manipulation is essentially hard-wired into an electromechanical system. For example, initial processing of an empty, or insufficiently full, sample container could generate a signal above a threshold value, and thereby cause a solenoid to kick the sample off from the processing conveyor.

Figure 4:
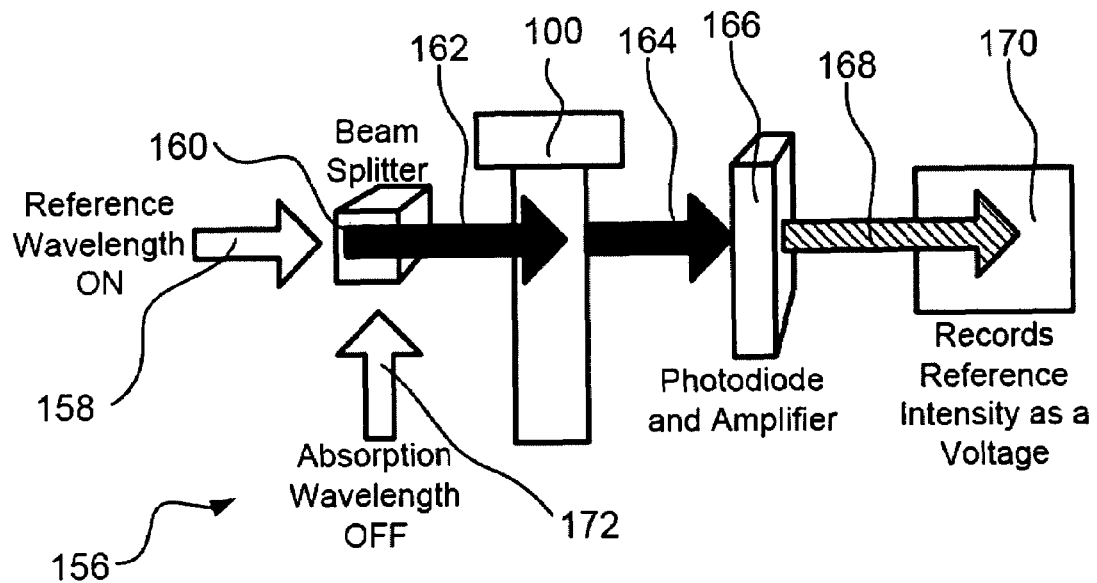
FIG. 4 is a schematic illustrating an alternative operable arrangement to collect data for practice of a method of use according to certain principles of the instant invention.

With reference now to FIG. 4, a portion of an operable fluid sample interrogation system constructed according to certain principles of the instant invention is indicated generally at 156. A first source of radiation 158 is arranged to apply a first radiation having a first characteristic wavelength (e.g. 980 nm) to beam splitter 160, which directs the first emitted radiation 162 toward a location on container 100. The first transmitted radiation 164 is detected by a detector, such as illustrated photo diode and amplifier arrangement 166. A signal 168, corresponding to the intensity of first transmitted radiation 164 can then be stored and/or manipulated in comparison structure, such as programmable integrated circuit 170, or a computer 152 (FIG. 3).

Figure 5:
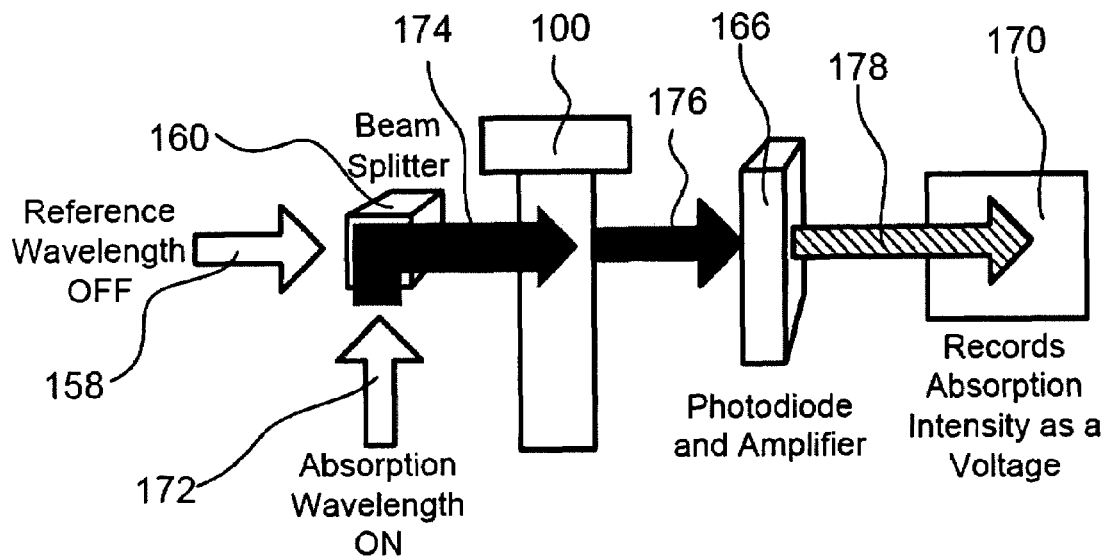
FIG. 5 is the same view illustrated in FIG. 4.

With reference now to FIG. 5, a second source of radiation 172 is energized, and source 158 is turned off. Source 172 is used to apply a second emitted radiation 174 having a second characteristic wavelength (e.g. 1550 nm) to beam splitter 160, and toward a location on container 100 (see, also, FIG. 4). Desirably, radiation 174 is directed toward the same location on container 100 that was contacted by radiation 162. In such case, the first and second transmitted radiation 164, 176, respectively, will pass through the same amount of fluid and structure, including any labels carried on the walls of container 100. Again, second transmitted radiation 176 is detected by a detector, such as the illustrated photo diode and amplifier arrangement 166. A second signal 178, corresponding to the intensity of transmitted radiation 176 can then be stored and/or manipulated in comparison structure, such as programmable integrated circuit 170, or a computer 152.

In general, one of the first or second source of radiation, 158 or 172, is selected having a characteristic wavelength for use as a reference and typically based upon its substantial lack of attenuation when transmitted through a known fluid composition. The other of the first and second source of radiation is selected having a characteristic wavelength that is distinguishable from the other radiation's wavelength and is used as a measurement tool based upon its predictive attenuation when transmitted through the same known fluid composition. Desirably, both first and second radiation will have wavelengths that permit transmission through the container walls and a number of labels that may be carried on such walls. Data manipulation or reduction, to determine one or more fluid characteristic, typically includes dividing a value corresponding to the intensity of one transmitted radiation by the value corresponding to the intensity of the other transmitted radiation. The result of such calculation is then compared to a predetermined value to make a determination of a fluid characteristic.

The absolute intensity of the transmitted light, however, cannot be used as a reliable measure of detection. There are other factors such as the labels on the outside of the test tube, the test tube material, and its wall thickness that affect the transmission of light. To exclude these variables from the measurement, and to obtain a signal that only relates to the measure of interest, it is necessary to implement a reference and an absorption light each at a given wavelength. The reference wavelength is selected in a region outside of the absorption band, while the absorption wavelength is selected from inside this band. Computing the ratio of the intensity between the reference and the absorption wavelength removes all disturbance factors and results in a signal that only relates to the measure of interest.

Figure 6:
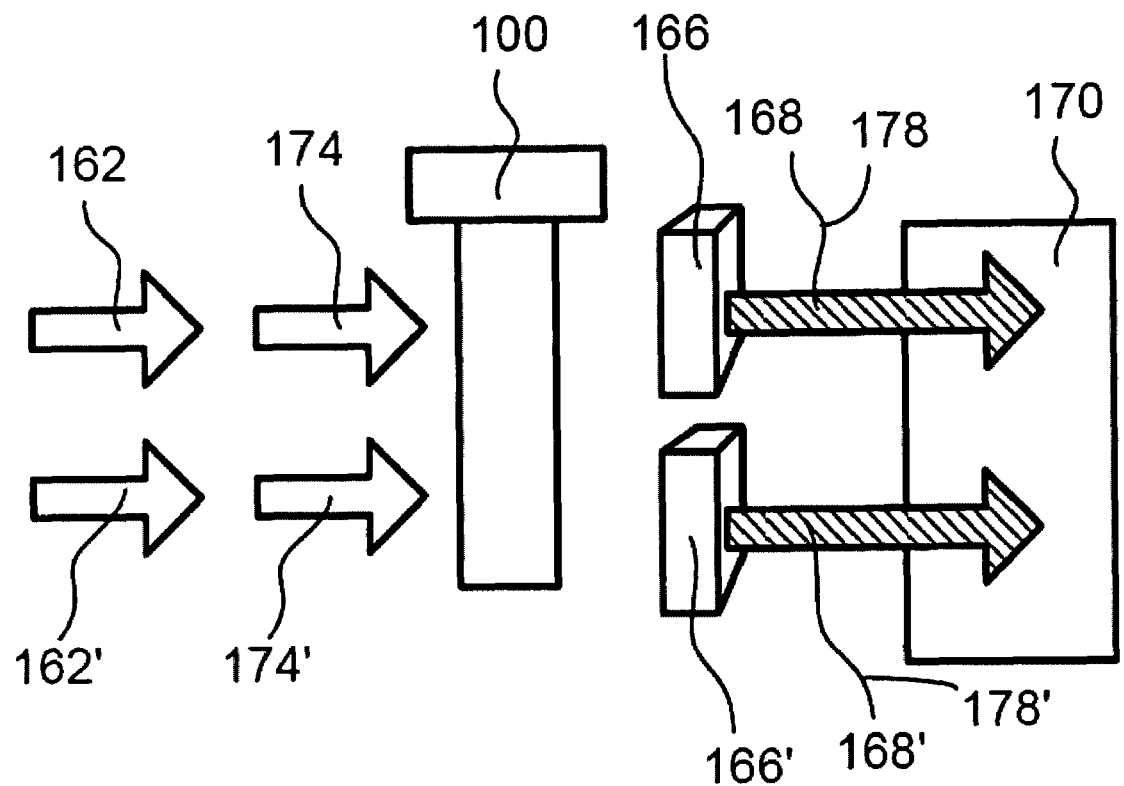
FIG. 6 is a schematic illustrating an alternative operable arrangement to collect data for practice of a method of use according to certain principles of the instant invention.

FIG. 6 illustrates an arrangement effective to interrogate a container 100 at two different elevations. Such may be useful, for example, in determining presence of a sufficient volume of fluid inside a container. As illustrated, emitted radiation including a reference characteristic wavelength 174 and an absorption characteristic wavelength 162 are applied to a container 100 at a first elevation. Again, such radiation is desirably directed to the same location on container 100 to eliminate container and label variation as a source of noise in the transmitted radiation and resulting signal produced by detector 166. Values for the transmitted radiation 168 and 178 are then available for data reduction in comparison structure, such as a comparison structure including programmable integrated circuit 170. At a second elevation, emitted radiation including a reference characteristic wavelength 174' and an absorption characteristic wavelength 162' are applied to the container 100. Again, such radiation is desirably directed to the same location on container 100 to eliminate container and label variation as a source of noise in the transmitted radiation and resulting signal produced by detector 166'. Values for the intensity of transmitted radiation 168' and 178' are then made available for data reduction and/or manipulation by comparison structure.

It is within contemplation that emitted measurement radiation 162 and 162' could be produced from the same source, such as a laser, LED, or assembly of a light source and filter arrangement. Similarly, emitted reference radiation 174 and 174' could also be from the same source. In such case, a known optical arrangement (e.g. including one or more mirror, beam splitter, lens, and the like), can be provided to direct such radiation to a plurality of desired elevations and locations. It is also within contemplation that a reference or measurement radiation source may be disposed at each desired interrogation elevation. In any case, a detector would be operably provided at the corresponding elevation. It is further within contemplation to displace a container 100 with respect to one or more sources or beams of radiation, effective to provide a plurality of elevations for use in interrogation of the container 100.

EXAMPLE 1

Detection of Fluid in a Container

Figure 7:
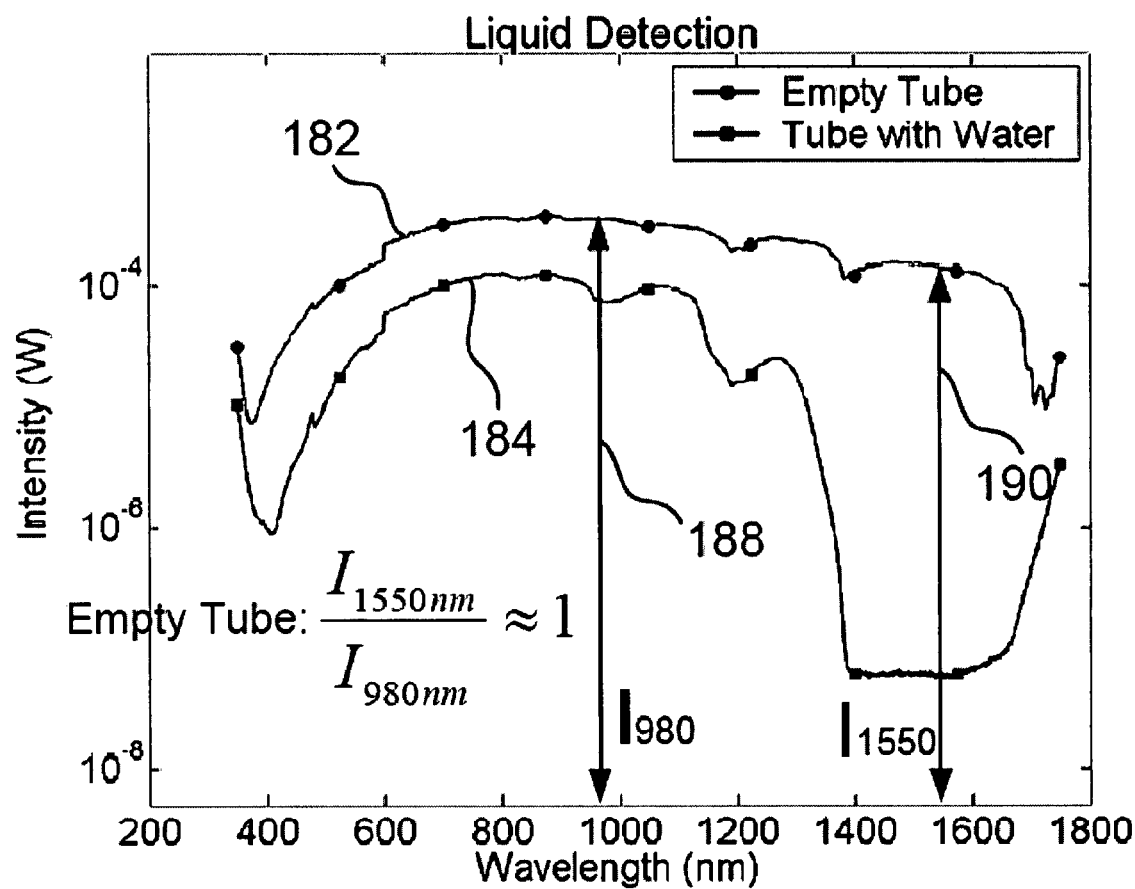
FIG. 7 is a plot illustrating detected intensity of transmitted radiation vs. wavelength of emitted radiation, and emphasizing data for use in computing an intensity ratio for an empty container.
Figure 8:
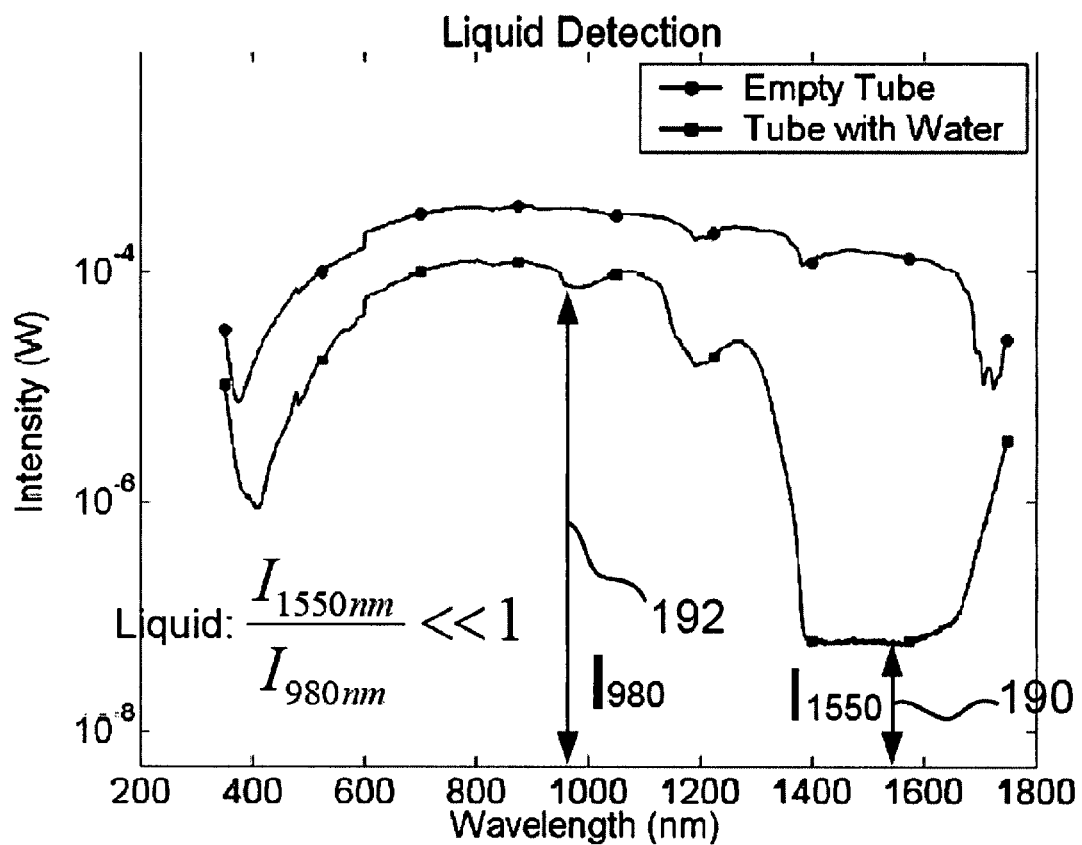
FIG. 8 is a plot illustrating detected intensity of transmitted radiation vs. wavelength of emitted radiation, and emphasizing data for use in computing an intensity ratio for a container including a fluid sample.

Using the configuration shown in FIG. 3, broad spectrum scans were performed to identify the transmission of light through an empty test tube 100 and tubes containing blood samples. As can be seen in FIGS. 7 and 8, for wavelengths from about 350-900 nm, the intensity contour 182 of the empty tube is essentially parallel to the intensity contour 184 of the filled tube, with lower intensities measured for the filled tube. Between about 1400 and 1600 nm, however, the intensity for the filled tube drops by three orders of magnitude, indicating that the blood sample absorbs light at these wavelengths significantly, while the empty tube shows no such behavior. As a result, presence of a blood fluid sample can be detected using the 1400-1600 nm spectrum.

However, there is an additional difficulty. Tubes are typically covered with labels of varying number that exhibit additional absorption, making it difficult, if not impossible, to detect volume simply based on absolute intensity of light at a specific wavelength. Instead it is advantageous to measure the intensity of transmitted light at two separate wavelengths at the same location on the test tube. A reference wavelength is selected in a region outside of the absorption spectrum whereas the measuring wavelength is selected in a region where absorption takes place. This is shown in FIGS. 7 and 8, where a characteristic reference wavelength of 980 nm is selected, and a characteristic measurement wavelength of 1550 nm is selected. The reference intensity 188 measured through an empty container is approximately the same magnitude as the measurement or interrogation intensity 190 measured through that container. In contrast, the reference intensity 192 measured through a container full of fluid is approximately three orders of magnitude greater than the interrogation intensity 194 measured through that fluid and container. By taking the ratio of the reference and interrogation intensities, all factors such as the material of the test tube, its wall thickness, type and number of labels, are eliminated from the measurement. The result of this data manipulation technique is shown in FIG. 9.

Figure 9:
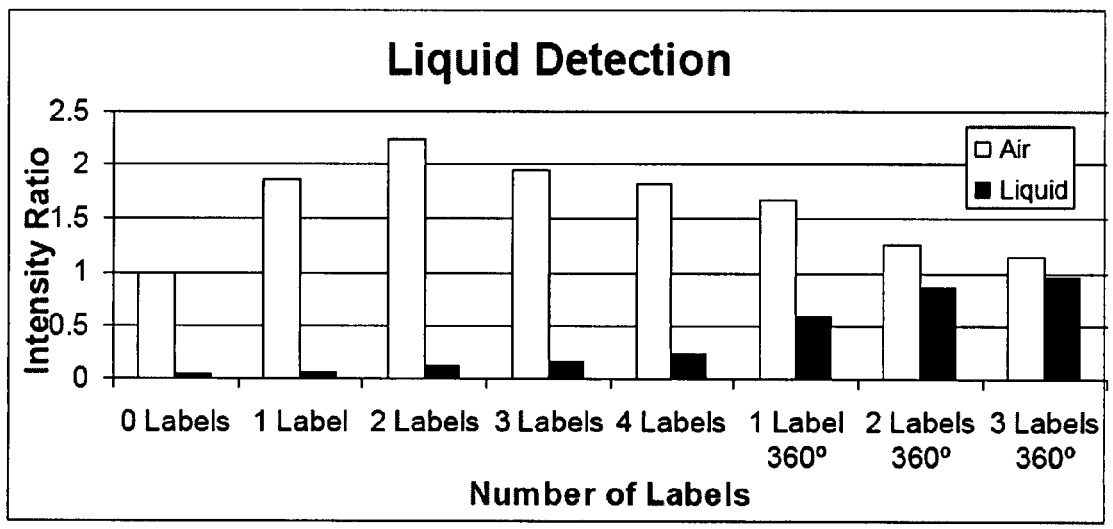
FIG. 9 is a bar chart illustrating detected intensity ratios of transmitted radiation through-containers that are empty and containers that contain a fluid sample, and contrasting such ratios for containers carrying a different number of labels.

As is apparent from FIG. 9, taking the ratios of the intensities at reference and absorption or interrogation wavelength creates an unambiguous signal that directly relates to the presence of a blood sample. In FIG. 9, the ratios are lower than those seen in FIG. 7 and FIG. 8. This is a result of the spectrum response of the photodiode used to detect the light intensity in an arrangement such as illustrated in FIGS. 4 and 5. The photodiode is able to detect significantly lower level of light than the spectrum analyzer. For all cases, an empty tube is indicated by an intensity ratio $I_{absorption}/I_{reference}$ of greater than 0.98. That same cut off factor can be used to predict filled samples where the minimum intensity ratio is 0.98.

With reference again to FIGS. 4 and 5, the system includes discrete light sources that emit light at 980 and 1550 nm, respectively, or any two lights that work as a reference and absorption pair. The light passes through a beam splitter 160 that directs the light of both sources through the test tube 100 at the same location. A photodiode receives the transmitted light and gives off a voltage 168, 178 that is a function of the transmitted light intensity. For volume or fluid detection, the system turns on one LED first (e.g. the 980 nm LED), but leaves the other 1550 nm LED off, and records the resulting voltage. Next, the 1550 nm LED is turned on, and the 980 nm LED is turned off, and the resulting voltage is recorded. The values of the two voltages are stored in a programmable integrated circuit (PIC), or programmable logical circuit (PLC), 170 and the ratio is computed.

EXAMPLE 2

Hemolysis Detection

Figure 10:
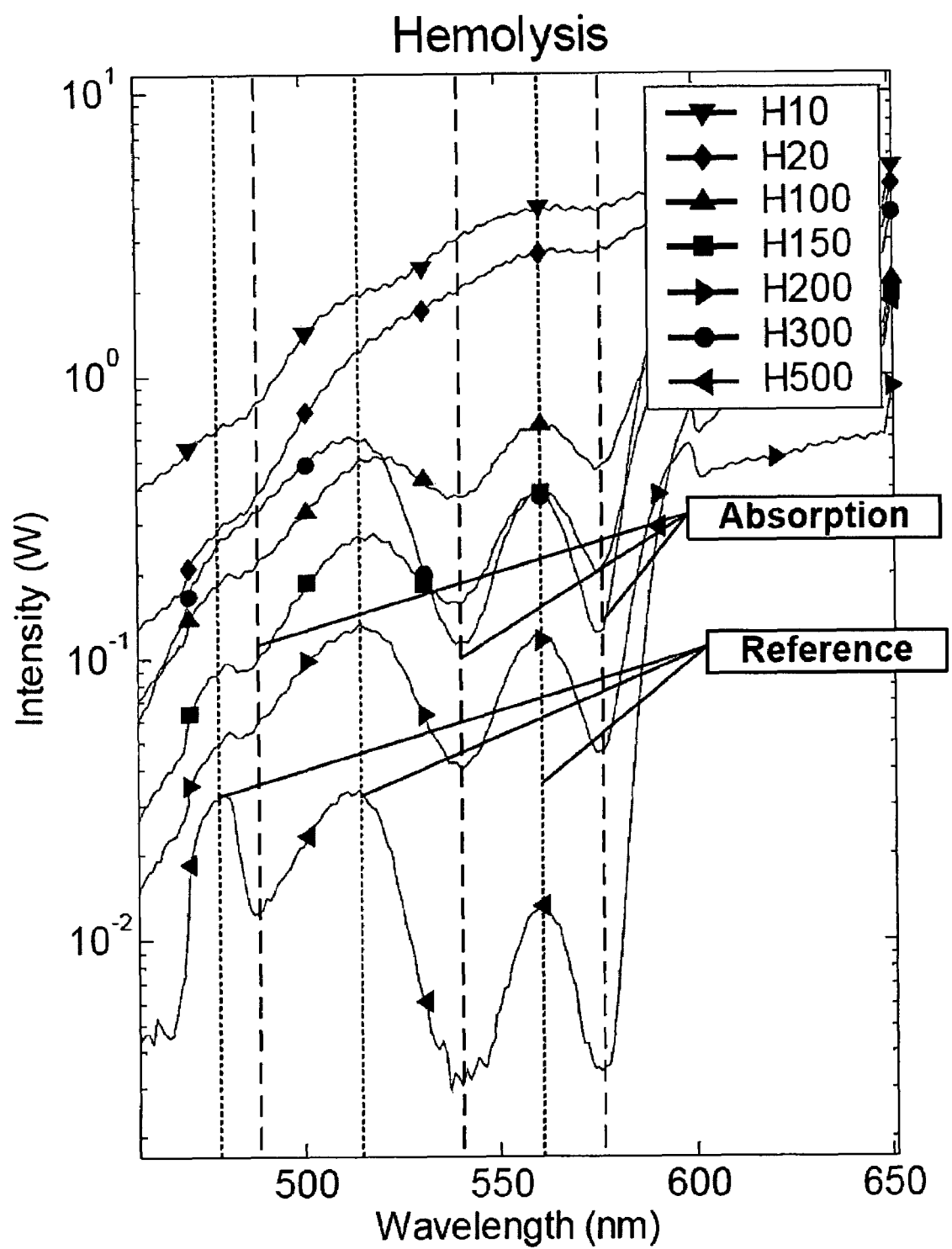
FIG. 10 is a plot of intensity vs. wavelength between 450 nm and 650 nm to illustrate varying levels of absorption due to hemolysis.

Blood samples sometimes contain varying levels of hemolysis, which trained technicians detect by the color of the sample. Using an interrogation setup such as illustrated in FIG. 3, a range of wavelengths where absorption due to hemolysis was found (see FIG. 10). There are three distinct wavelengths where hemolysis causes the loss of light: 488 nm, 540 nm, and 575 nm. There is a strong correlation between the absorption of light and the level of hemolysis at those wavelengths. Useful reference wavelengths for hemolysis include 480 nm, 515 nm, and 560 nm.

Figure 11:
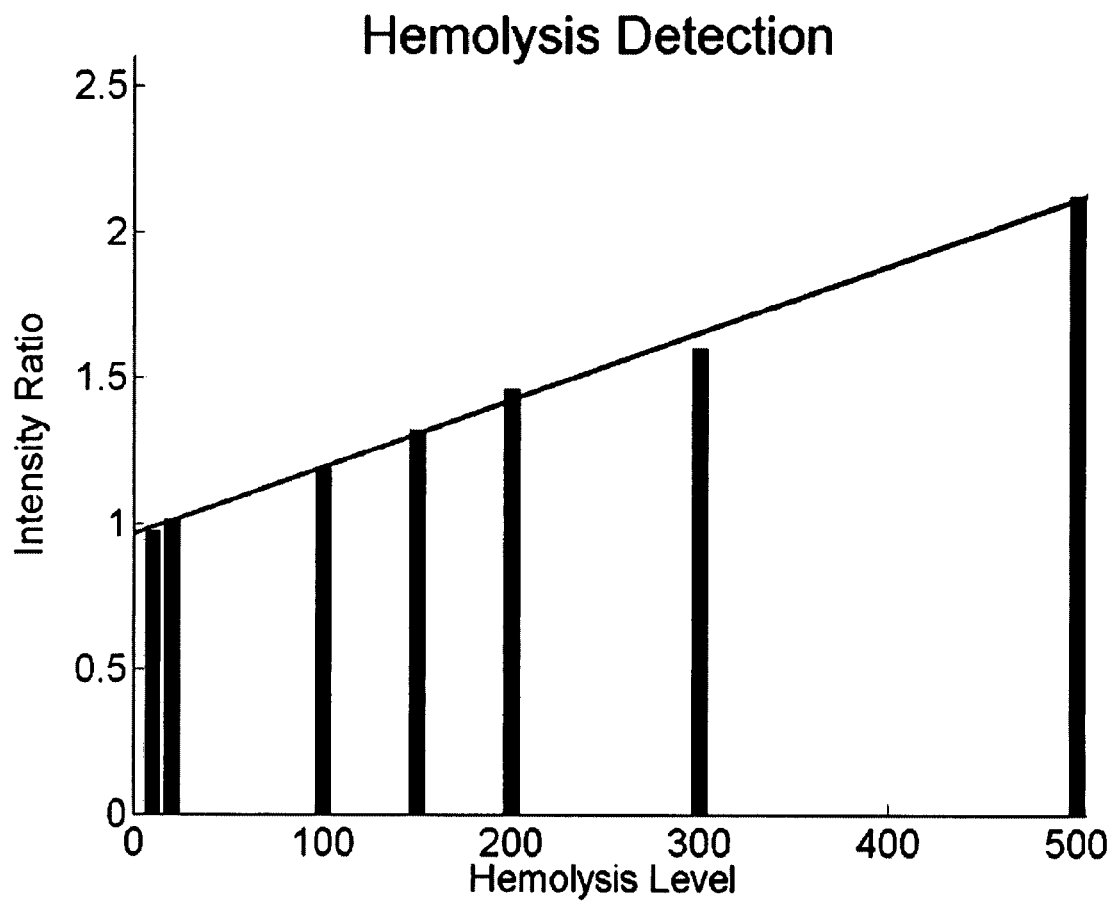
FIG. 11 is a plot of ratio of intensity of transmitted radiation vs. hemolysis level for potential use in quantifying hemolysis in a sample.

To detect the level of hemolysis and to eliminate the effects of paper labels, tube material, wall thickness, intensity ratios based on absorption and reference wavelengths can be computed. In reality, however, light sources such as light-emitting diodes (LEDs) are only available at certain wavelengths that may not necessarily match exactly the regions shown in FIG. 10. Based on the absorption spectrum in FIG. 10 and commercially available LEDs, intensity ratios for each level of hemolysis were computed and a best line fit was calculated for each possible combination of wavelengths. FIG. 11 shows a combination that satisfies the following conditions:

1. the minimum slope of the best line fit exceeds 0.001 (yields a 50% change from lowest to highest signal);

2. the relative change between the smallest and largest value is at least 50%; and 3. the worst data fit does not exceed 9.5%.

Combining a 565 nm with a 570 nm LED from Table 1 as shown in FIG. 11 yields a very linear correlation between the intensity ratio and the level of hemolysis.

EXAMPLE 3

Lipemia Detection

Another frequently encountered interference in blood samples is lipemia. Low levels of lipemia can be tolerated in the sample. At higher levels, however, the presence of lipemia interferes with the results of the analyzers. A white light source and interrogation setup such as illustrated in FIG. 3 produced the intensity spectrum shown in FIG. 12, and shows two regions of interest. Compared to the intensity at 880 nm, the amount of transmitted light at a wavelength of 951 nm drops off sharply with increasing levels of lipemia. This indicates that lipemia effectively absorbs light at 951 nm (absorption wavelength) but is relatively transparent at 880 nm (reference wavelength).

Figure 12:
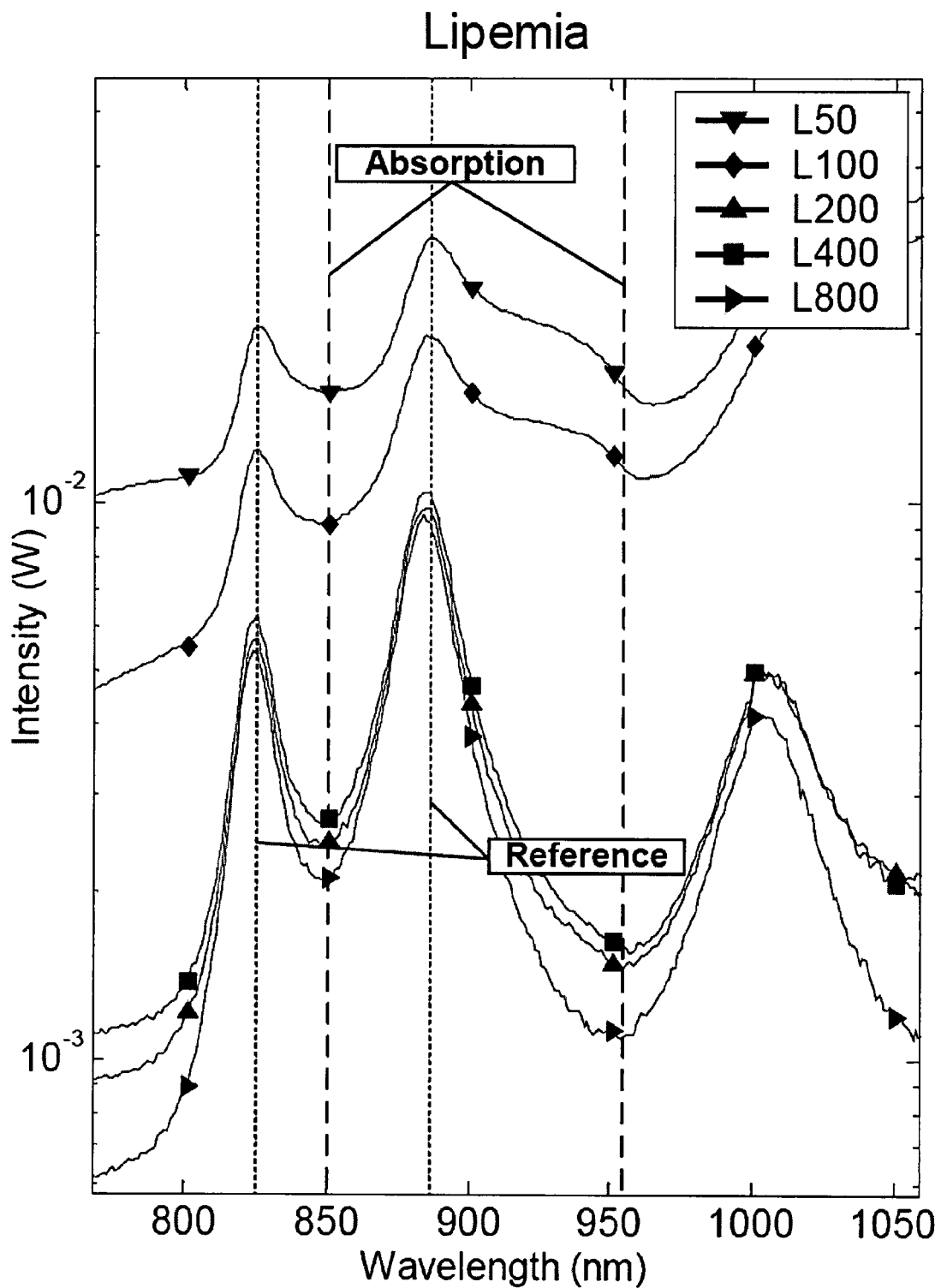
FIG. 12 is a plot of intensity vs. wavelength between 800 nm and 1050 nm to illustrate various levels of absorption due to lipemia.
Figure 13:
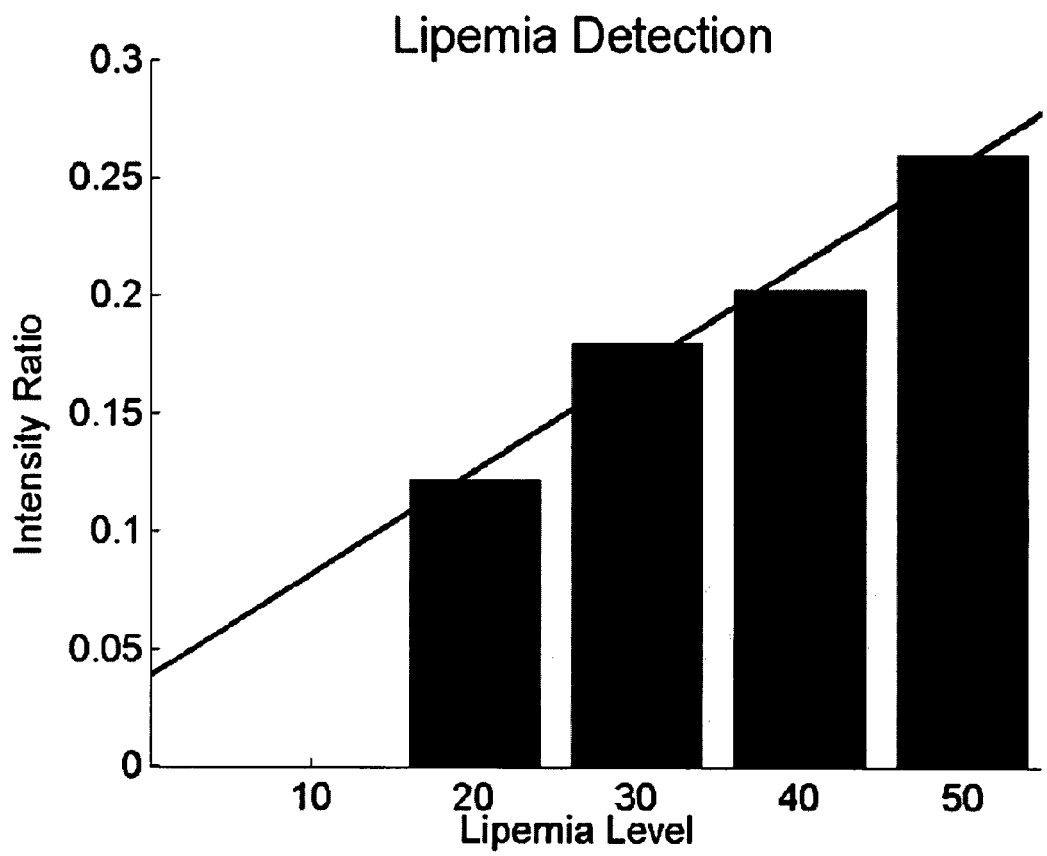
FIG. 13 is a plot of ratio of intensity of transmitted radiation vs. lipemia concentration for potential use in quantifying lipemia in a sample.

Based on the white light spectrum shown in FIG. 12, combinations of commercially available LEDs presented in Table 2 were examined and their intensity ratios were computed. The combination of 351 nm and 370 nm produces a nearly perfectly linear correlation between the intensity ratios and the levels of lipemia with errors of less than 6%, as seen in FIG. 13. This combination satisfies the following conditions:

1. the minimum slope of the best line fit exceeds 0.055;
2. the relative change between the smallest and largest value is at least 50%;
3. the worst data fit does not exceed 8.5%.

EXAMPLE 4

Icterus Detection

Figure 14:
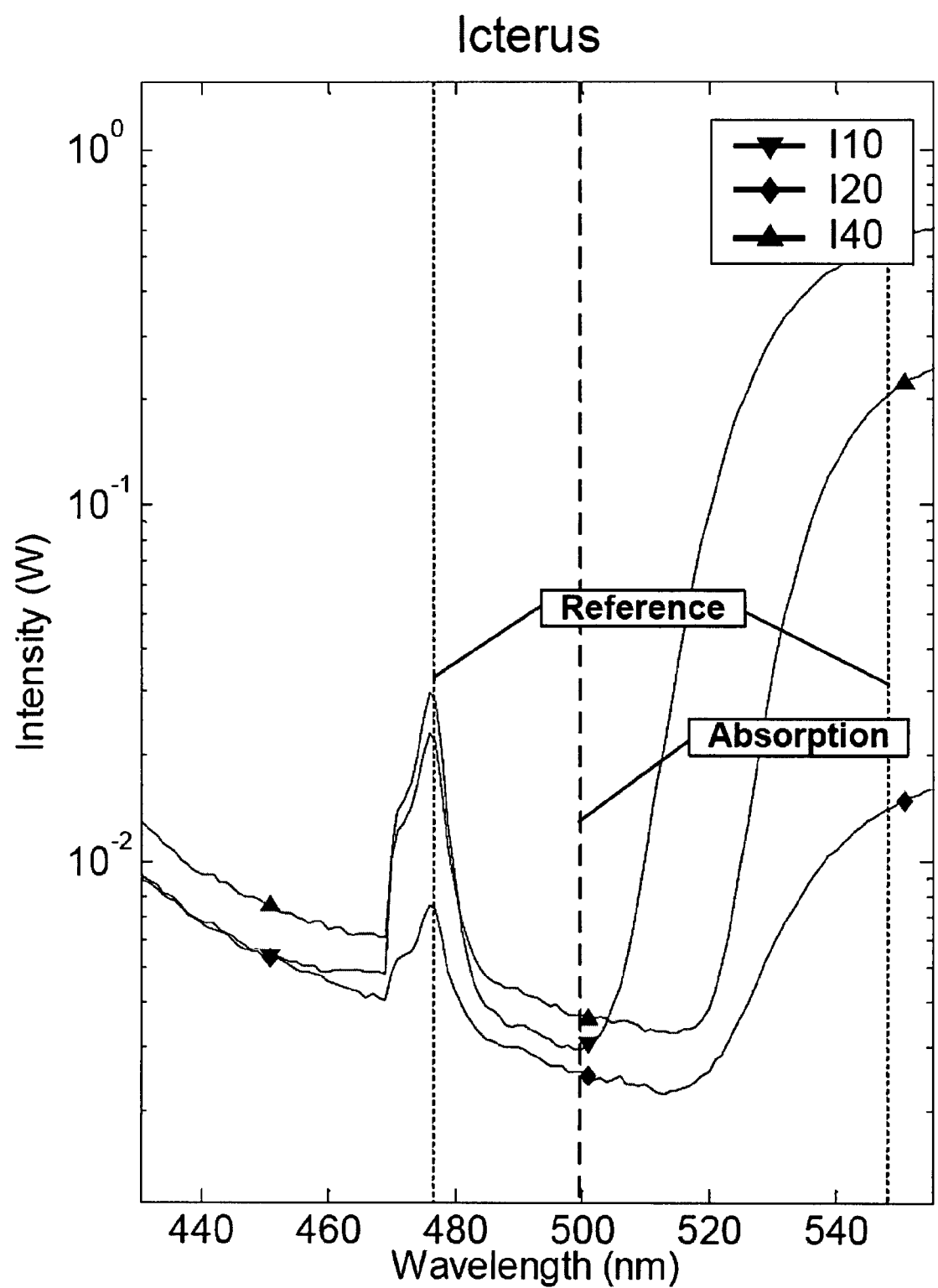
FIG. 14 is a plot of intensity vs. wavelength, emphasizing a portion between 440 nm and 540 nm to illustrate various levels of absorption due to icterus.

The white light spectrum of blood samples containing various levels of icterus are shown in FIG. 14. Workable reference and absorption wavelengths may be selected from the plotted data.

EXAMPLE 5

Urine Detection

Figure 15:
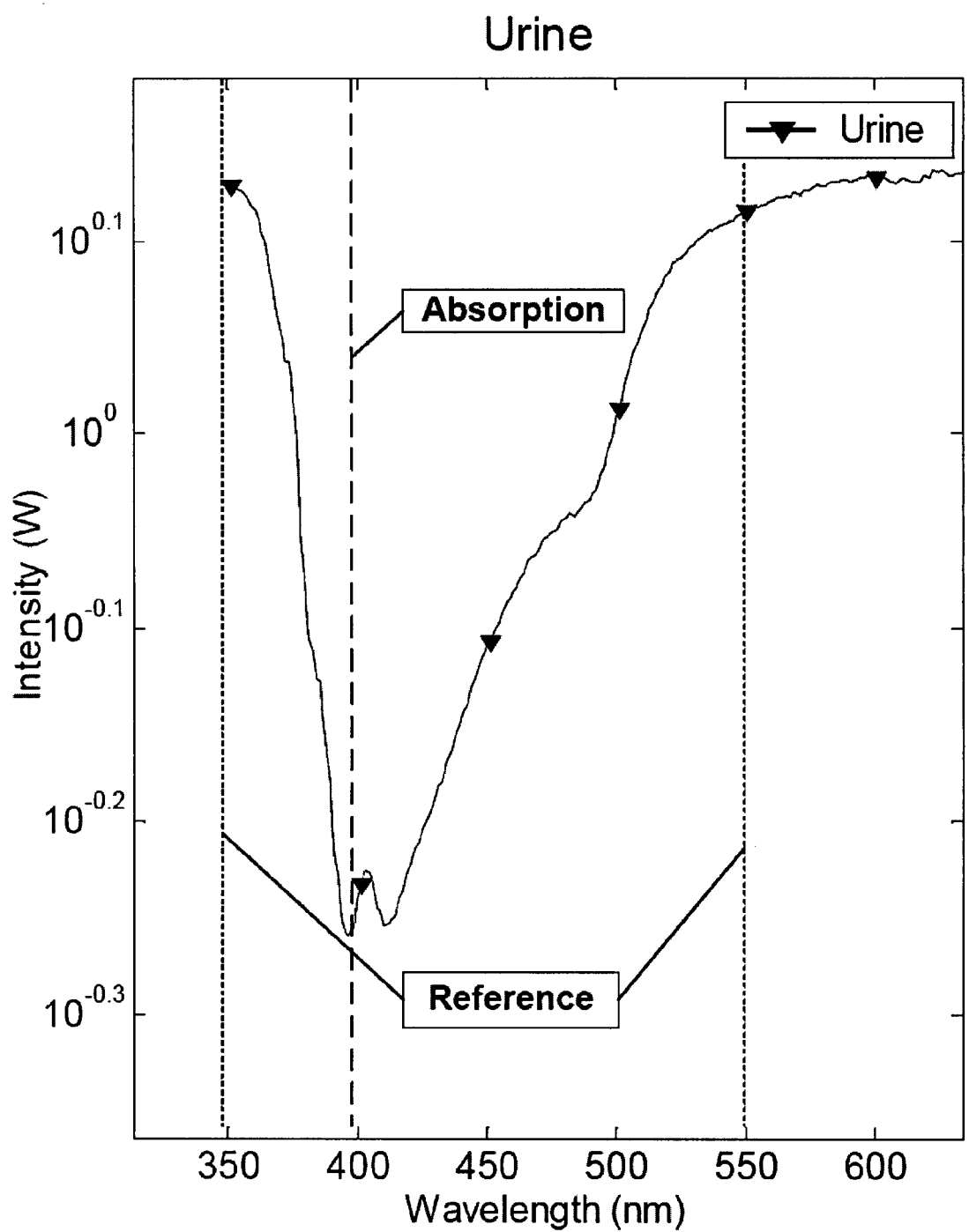
FIG. 15 is a plot of intensity vs. wavelength between 350 nm and 600 nm to illustrate various levels of absorption due to urine.

Urine can easily be confused with blood serum because of their similar color. As such, having the ability to detect urine with an automated detection system is important. The white light spectrum illustrated in FIG. 15 shows a small amount of absorption at 400 nm. An operable reference wavelength for an optical system could be located at 550 nm.

EXAMPLE 6

Anticoagulant EDTA

Figure 16:
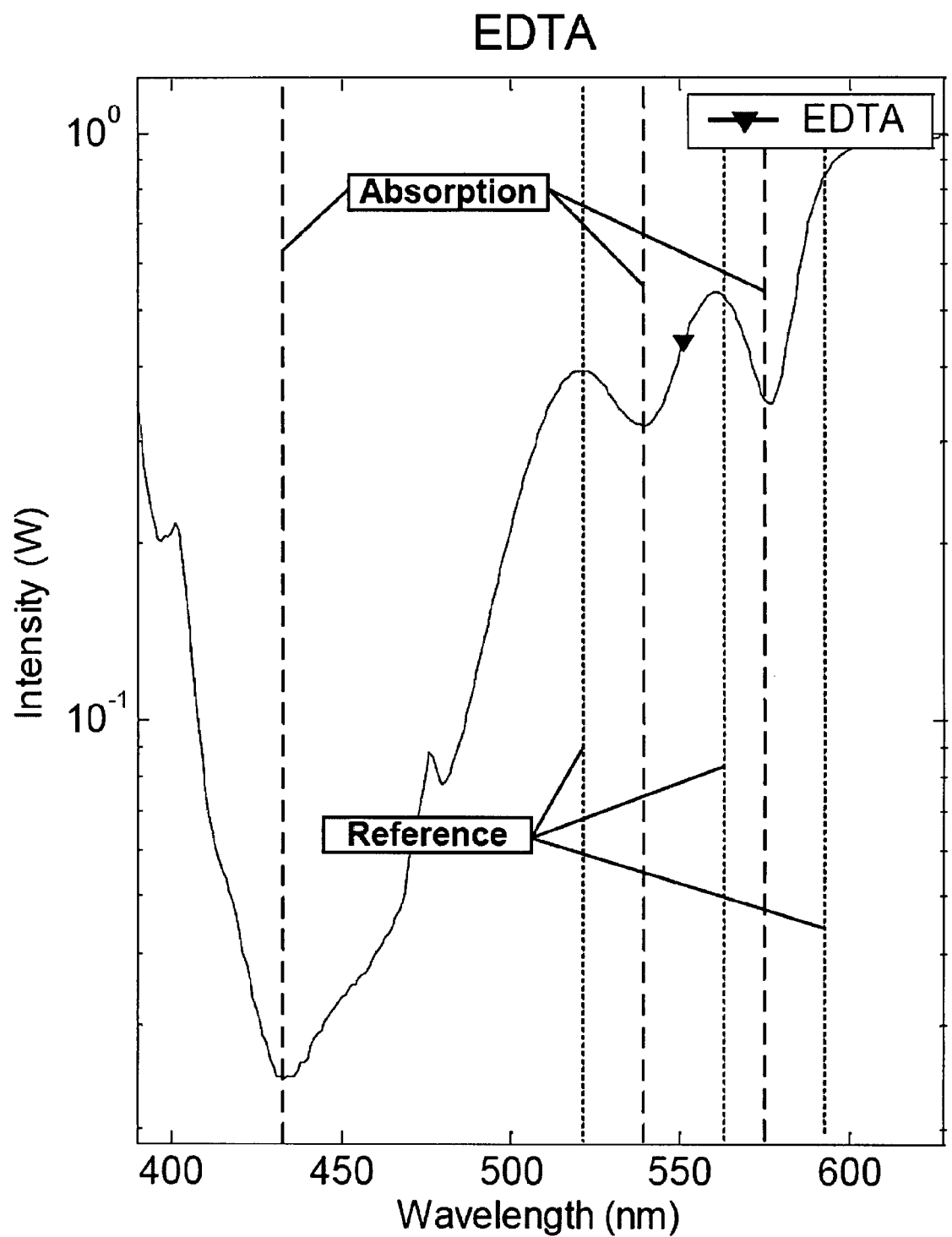
FIG. 16 is a plot of intensity vs. wavelength between 400 nm and 600 nm to illustrate various levels of absorption due to anticoagulant EDTA.

The presence of anticoagulant agents can affect results from blood analysis tests, so screening for such anticoagulant may be important. The white light spectrum illustrated in FIG. 16 shows a small amount of absorption at 440 nm, 540 nm, and 575 nm. Operable reference wavelengths for an optical system could be located at 520 nm, 560 nm, and 600 nm.

EXAMPLE 7

Cerebral Spinal Fluid (CFS)

Figure 17:
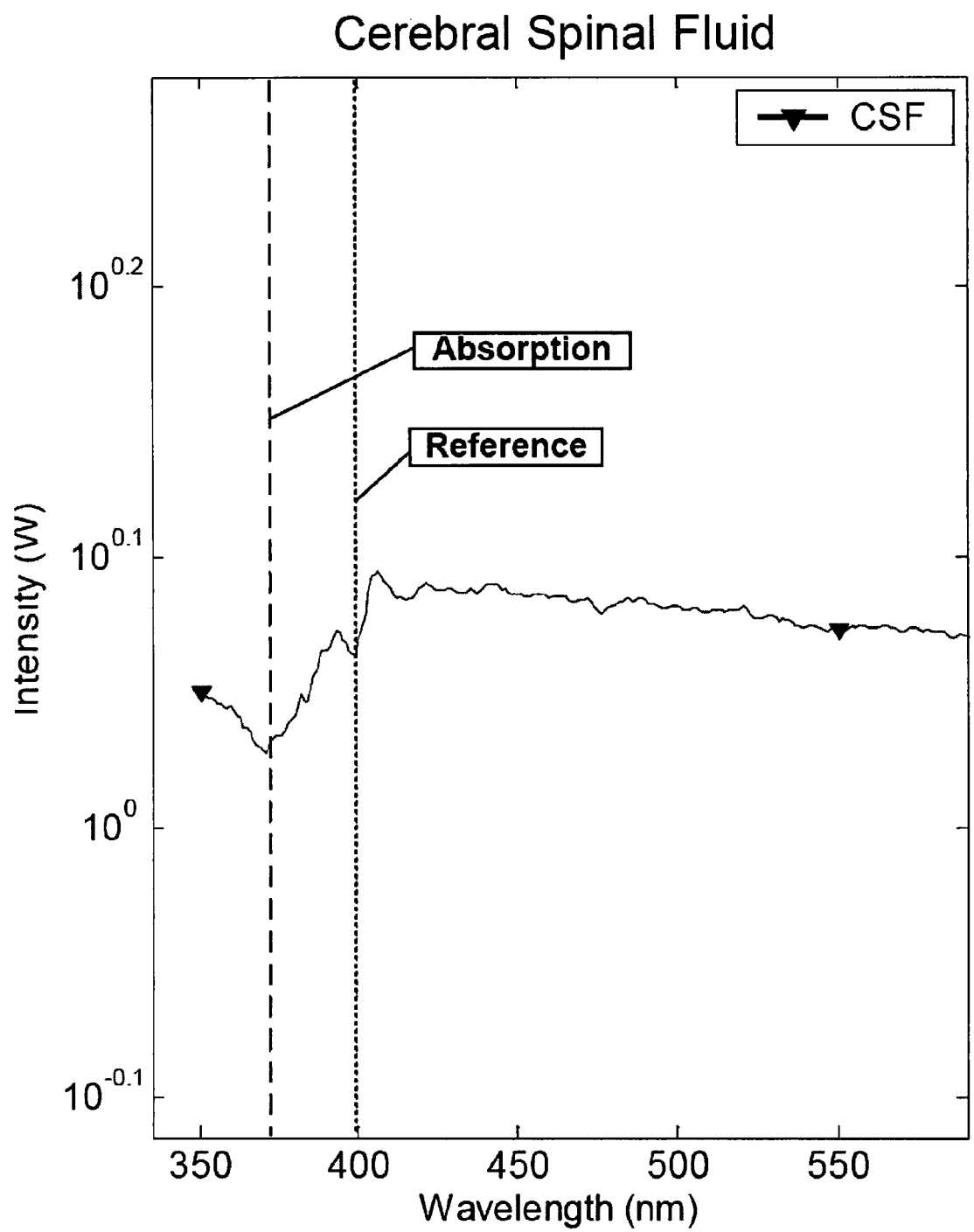
FIG. 17 is a plot of intensity vs. wavelength between 350 nm and 550 nm to illustrate various levels of absorption due to cerebral spinal fluid (CSF)

The white light spectrum illustrated in FIG. 17 shows a small amount of absorption related to CFS at 375 nm. An operable reference wavelength for an optical system could be located at 400 nm.

EXAMPLE 8

Full Spectrum

Figure 18:
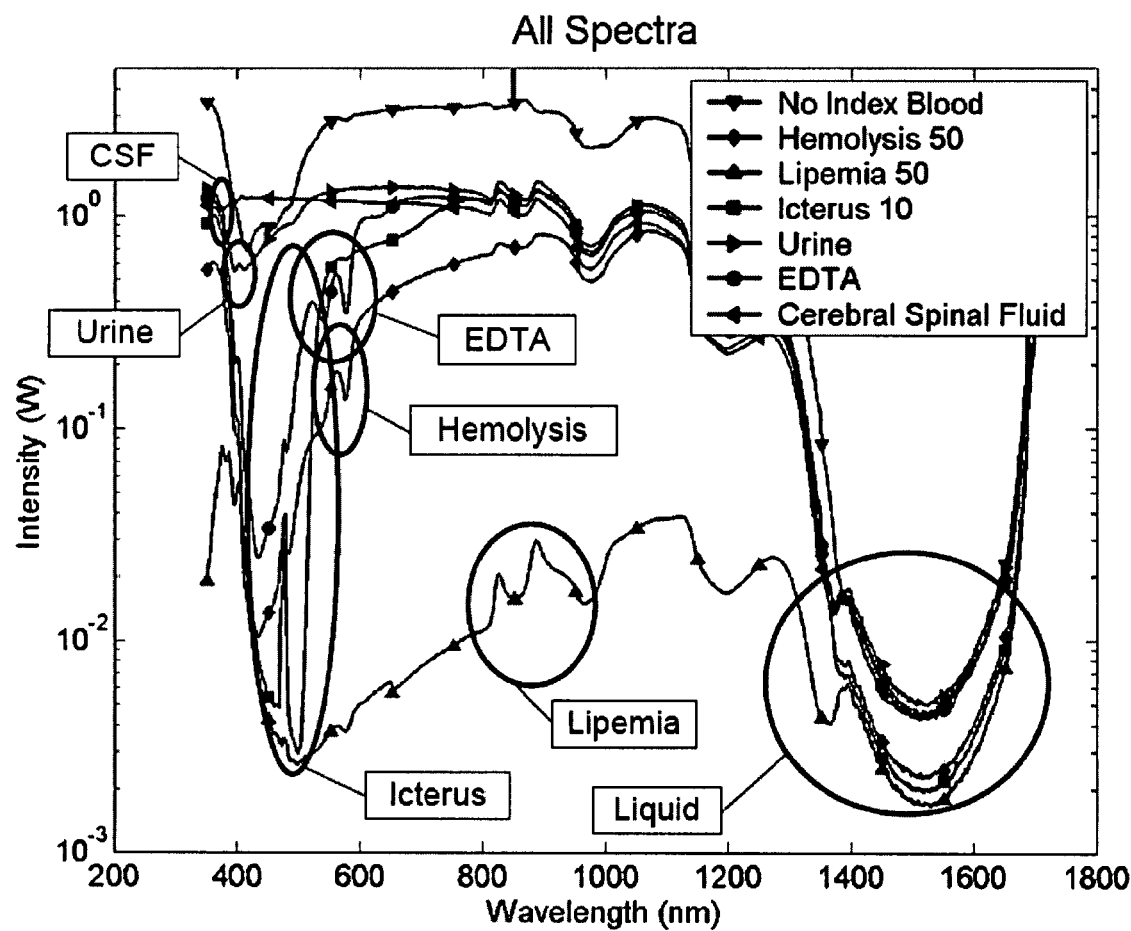
FIG. 18 is a plot of intensity vs. wavelength, illustrating zones of interest for identifying a particular characteristic in an assortment of fluids.

FIG. 18 illustrates an overlay of intensity vs. wavelength for all data discussed above, and points out zones of interest for identifying a particular characteristic in an assortment of fluids.

What is claimed is:

1. An apparatus, adapted to interrogate a fluid specimen through the walls of a container in which the fluid is held, said apparatus comprising:
    a first radiation structure configured and arranged to direct a first emitted radiation through said container at a first location for reception by a first intensity detector to obtain a first transmitted intensity, said first emitted radiation comprising a characteristic first wavelength that permits transmission of said first emitted radiation through said walls of said container and at least one label that may be attached thereto, said characteristic first wavelength selected as a reference based upon its substantial lack of attenuation when transmitted through a known fluid composition;
    a second radiation structure configured and arranged to direct a second emitted radiation through said container at said first location for reception by said first intensity detector to obtain a second transmitted intensity, said second emitted radiation comprising a characteristic second wavelength that permits transmission of said second emitted radiation through said walls of said container and at least one label that may be attached thereto and is distinguishable from said characteristic first wavelength, said characteristic second wavelength selected as a measurement tool based upon its predictive attenuation when transmitted through said known fluid composition; and
    a comparison structure adapted to compare a first intensity ratio of said first transmitted intensity and said second transmitted intensity against a predetermined value.

2. The apparatus according to claim 1, wherein:
    said intensity ratio comprises division of said first transmitted intensity by said second transmitted intensity.

3. The apparatus according to claim 1, wherein:
    said intensity ratio comprises division of said second transmitted intensity by said first transmitted intensity.

4. The apparatus according to claim 1, further comprising:
    a third radiation structure configured to direct a third emitted radiation through said container at a second location to obtain a third transmitted intensity, said second location being disposed at a container elevation that is different from said first location;
    a fourth radiation structure configured to direct a fourth emitted radiation through said container at said second location to obtain a fourth transmitted intensity; and wherein said comparison structure is further adapted to compare first data, comprising said second transmitted intensity, to second data, comprising said fourth transmitted intensity, to indicate a presence of a desired fluid level in said container.

5. The apparatus according to claim 4, wherein:
said comparison structure is further adapted to compare said first intensity ratio against a second intensity ratio of said third transmitted intensity and said fourth transmitted intensity to indicate said presence of a desired fluid level in said container.

6. The apparatus according to claim 4, wherein said apparatus further comprises:
a second beam splitter, said second beam splitter configured to cast said third emitted radiation and said fourth emitted radiation onto said second location.

7. The apparatus according to claim 4, wherein:
said third emitted radiation comprises said characteristic first wavelength and said fourth emitted radiation comprises said characteristic second wavelength.

8. The apparatus according to claim 4, wherein:
said third transmitted radiation and said fourth transmitted radiation are received by a second intensity detector.

9. A method for using the apparatus according to claim 4, comprising:
disposing said container in position for interrogation by radiation;
separately applying said first emitted radiation and said second emitted radiation, in any order, to said first location;
obtaining a first numeric value corresponding to said first transmitted radiation and a second numeric value corresponding to said second transmitted radiation;
separately applying said third emitted radiation and said fourth emitted radiation, in any order, to said second location;
obtaining a third numeric value corresponding to said third transmitted radiation and a fourth numeric value corresponding to said fourth transmitted radiation;
calculating a first ratio of said first numeric value and said second numeric value; and
comparing said first ratio to a predetermined value to make a determination about a fluid characteristic.

10. The method according to claim 9, further comprising:
calculating a second ratio of said third numeric value and said fourth numeric value; and
comparing said first ratio to said second ratio to make a determination about a fluid characteristic.

11. The apparatus according to claim 1, further comprising:
an emission-directing structure adapted to move said container relative to said first intensity detector to permit said first intensity detector to detect said first emitted radiation and said second emitted radiation transmitted through said container at a second location, said second location being disposed at a container elevation that is different from said first location, to verify a desired fluid level in said container.

12. The apparatus according to claim 1, wherein said apparatus further comprises:
a first beam splitter, said first beam splitter configured to cast said first emitted radiation and said second emitted radiation onto said first location.

13. A method for using the apparatus according to claim 1, comprising:
disposing said container in position for interrogation by radiation;
separately applying said first emitted radiation and said second emitted radiation, in any order, to said first location;
obtaining a first numeric value corresponding to said first transmitted radiation and a second numeric value corresponding to said second transmitted radiation;
calculating a first ratio of said first numeric value and said second numeric value; and
comparing said first ratio to a predetermined value to make a determination about a fluid characteristic.

14. The method according to claim 13, wherein calculating a first ratio comprises:
dividing said first numeric value by said second numeric value.

15. The method according to claim 13, wherein calculating a first ratio comprises:
dividing said second numeric value by said first numeric value.

16. An apparatus adapted to interrogate a fluid specimen contained inside a closed container, the apparatus comprising:
a first radiation source adapted to emit radiation comprising a reference wavelength that permits transmission of a first emitted radiation through said container and at least one label that may be attached thereto, said first radiation source being configured to direct said first emitted radiation through a first beam splitter to cast said first emitted radiation through a first location of said container for reception by a first intensity detector to obtain a first transmitted intensity;
a second radiation source adapted to emit radiation comprising a measurement wavelength that permits transmission of a second emitted radiation through said container and at least one label that may be attached thereto and is distinguishable from said reference wavelength, said second radiation source being configured to direct said second emitted radiation through said first beam splitter to cast said second emitted radiation through said first location of said container for reception by said first intensity detector to obtain a second transmitted intensity; and
a comparison structure adapted to compare a first intensity ratios of said first transmitted intensity and said second transmitted intensity against a predetermined value.

17. The apparatus according to claim 16, wherein:
said intensity ratio comprises division of said first transmitted intensity by said second transmitted intensity.

18. The apparatus according to claim 16, wherein:
said intensity ratio comprises division of said second transmitted intensity by said first transmitted intensity.

19. The apparatus according to claim 16, wherein:
said first radiation source is configured to direct said first emitted radiation through a second beam splitter to cast said first emitted radiation through a second location of said container for reception by a second intensity detector to obtain a third transmitted intensity;
said second radiation source is configured to direct said second emitted radiation through said second beam splitter effective to cast said second emitted radiation through said second location of said container for reception by said second intensity detector to obtain a fourth transmitted intensity; and
said comparison structure is further adapted to compare said first intensity ratio against a second intensity ratio, of said third transmitted intensity and said fourth transmitted intensity to indicate a presence of a desired fluid level in said container.

20. The apparatus according to claim 16, further comprising:
- a third radiation source adapted to emit radiation comprising a second reference wavelength that permits transmission of a third emitted radiation through said container and at least one label that may be attached thereto, said third radiation source being configured to direct said third emitted radiation through a second beam splitter to cast said third emitted radiation through a second location of said container for reception by a second intensity detector to obtain a third transmitted intensity;
- a fourth radiation source adapted to emit radiation comprising a second measurement wavelength that permits transmission of a fourth emitted radiation through said container and at least one label that may be attached thereto and is distinguishable from said second reference wavelength, said fourth radiation source being configured to direct said fourth emitted radiation through said second beam splitter to cast said fourth emitted radiation through said second location of said container for reception by said second intensity detector to obtain a fourth transmitted intensity; and
- said comparison structure is further adapted to compare said first intensity ratio against a second intensity ratio of said third transmitted intensity and fourth transmitted intensity to indicate a presence of a desired fluid level in said container.

21. An apparatus, adapted to interrogate a fluid specimen through the walls of a container in which the fluid is held, said apparatus comprising:

- radiation means adapted to direct a first emitted radiation and a second emitted radiation through said container;
- intensity detection means adapted to obtain:
  - a first value; for a first transmitted intensity resulting from said first emitted radiation passing through said container; and
  - a second value; for a second transmitted intensity resulting from said second emitted radiation passing through said container;
- comparison means adapted to compare a first intensity ratio, of said first value and said second value against a standard;
- wherein said first emitted radiation comprises a characteristic first wavelength that permits transmission of said first emitted radiation through said walls of said container and at least one label that may be attached thereto and is selected as a reference based upon its substantial lack of attenuation when transmitted through a known fluid composition; and
- wherein said second emitted radiation comprises a characteristic second wavelength that permits transmission of said second emitted radiation through said walls of said container and at least one label that may be attached thereto and is distinguishable from said characteristic first wavelength, said characteristic second wavelength selected as a measurement tool based upon its predictive attenuation when transmitted through said known fluid composition.

* * * * *